(12) United States Patent
Bracht

(10) Patent No.: US 6,308,560 B1
(45) Date of Patent: Oct. 30, 2001

(54) METHOD AND DEVICE FOR DETERMINING ADHESIVE PERFORMANCE OF FLAT ADHESIVE PRODUCTS ON THE SKIN OF HUMANS OR MAMMALS

(75) Inventor: Stefan Bracht, Ochttendung (DE)

(73) Assignee: LTS Lohman Therapie-Systeme GmbH, Neuwied (DE)

( * ) Notice: Subject to any disclaimer, the term of this patent is extended or adjusted under 35 U.S.C. 154(b) by 0 days.

(21) Appl. No.: 09/403,280

(22) PCT Filed: Mar. 31, 1998

(86) PCT No.: PCT/EP98/01869

§ 371 Date: Feb. 1, 2000

§ 102(e) Date: Feb. 1, 2000

(87) PCT Pub. No.: WO98/46980

PCT Pub. Date: Oct. 22, 1998

(30) Foreign Application Priority Data

Apr. 16, 1997 (DE) ............................................. 197 15 747

(51) Int. Cl.$^7$ ................................................... G01B 21/08
(52) U.S. Cl. ............................................................. 73/150 R
(58) Field of Search ............................ 73/827, 835, 838, 73/842, 150 R, 150 A

(56) References Cited

U.S. PATENT DOCUMENTS

| | | |
|---|---|---|
| 4,194,392 | * 3/1980 | Lombard et al. ................. 73/150 A |
| 4,856,325 | * 8/1989 | Tomita et al. ..................... 73/150 A |
| 5,388,442 | * 2/1995 | Kumar et al. ............................. 73/10 |
| 6,000,284 | * 12/1999 | Shin et al. ......................... 73/150 R |

\* cited by examiner

*Primary Examiner*—Max Noori
(74) *Attorney, Agent, or Firm*—Ann W. Speckman; James E. Klaniecki

(57) ABSTRACT

A process for ascertaining the adhesive behaviour of pressure-sensitive adhesive flat materials such as medicinal adhesive tape and, in particular, pressure-sensitive adhesive application systems such as transdermal therapeutic systems (TTS) is characterized in that a flat material (5) with an adhesive layer (6) of a defined coating weight per unit area and of defined quality of the adhesive mass is adhered with predetermined surface pressure and at a predetermined temperature to an elastic carrier film (4) of defined thickness and elasticity, and that said carrier film (4) is clamped into a test cell (21), in the manner of a membrane, between half-shells (1,2) of a test cell (21), and that the carrier film (4) along with the adhered flat material (5) is subjected, in chronologically repeated sequence, to loading and unloading with alternating elastic stretchings by defined loading forces from the side facing away from the flat material, and that a detachment of the adhesive layer, which detachment arises progressively per unit of time, is observed and qualitatively and/or quantitatively evaluated.

22 Claims, 3 Drawing Sheets

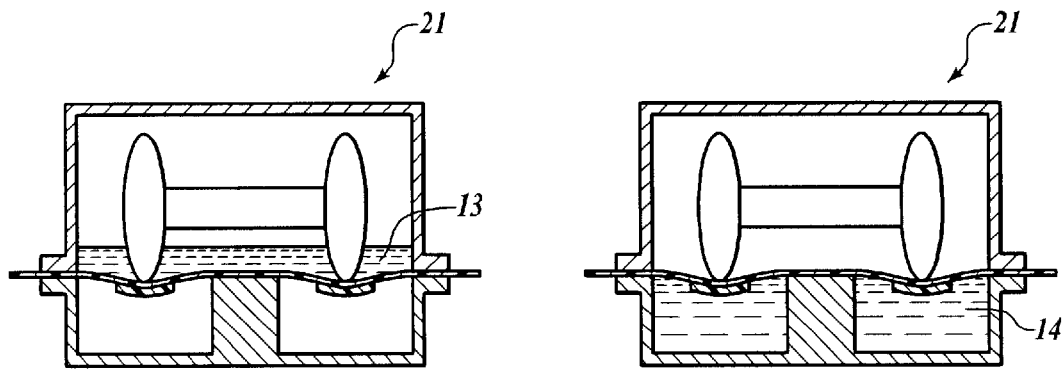
*Fig. 4.*      *Fig. 5.*
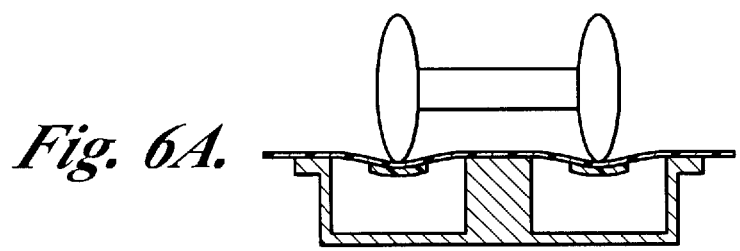
*Fig. 6A.*
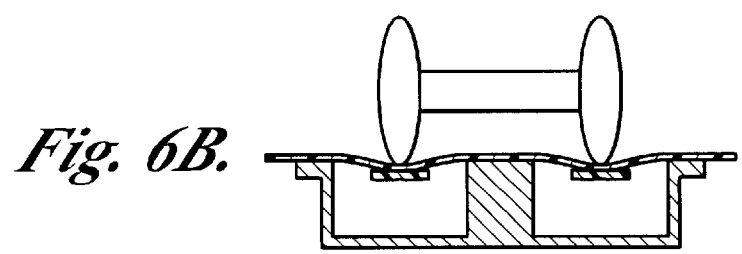
*Fig. 6B.*
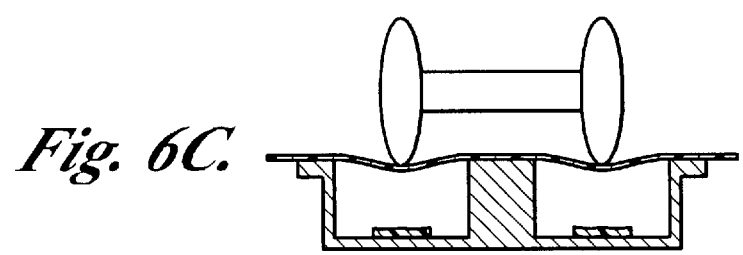
*Fig. 6C.*
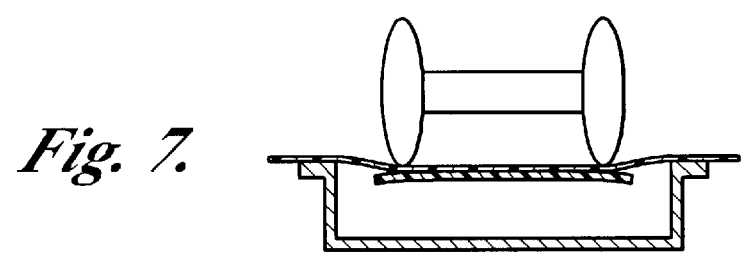
*Fig. 7.*

METHOD AND DEVICE FOR DETERMINING ADHESIVE PERFORMANCE OF FLAT ADHESIVE PRODUCTS ON THE SKIN OF HUMANS OR MAMMALS

TECHNICAL FIELD OF THE INVENTION

The invention relates to a process and a device for ascertaining the adhesive behaviour of pressure-sensitive adhesive flat materials such as medicinal adhesive tape and, in particular, pressure-sensitive adhesive application systems such as transdermal therapeutic systems (TTS), on the skin of humans or mammals.

The temporary connection by means of pressure-sensitive adhesive bonding comprises a period of time from a few hours up to 14 days. The term skin also comprises the mucosa of the upper air passages, of the eye and of the sexual organs.

The products addressed here are medicinal adhesive tapes for the purpose of fixation, or for wound treatment ("adhesive patches"). Further comprised are application systems adhering to the skin by pressure-sensitive adhesion, which means pharmaceutical products releasing one or more active substances or test substances primarily from an adhesive layer to the skin, or through the skin to the body. As an alternative, such systems can also be utilised to absorb chemical substances from the body through the skin. Such an application is useful for diagnostic purposes or for detoxication. In particular, the process and the device according to the invention relate to transdermal therapeutic systems (TTS) for the controlled, long-term release of one or more active substances to the skin. The distribution of these substances may be locally restricted, or extend to the entire organism of the subject wearing the system. TTSs are known to experts in the pharmaceutical field and are commercially available in large numbers.

The invention is especially suitable as a means for studying the pressure-sensitive adhesiveness of such products on the skin, especially when the products are being worn for prolonged periods of time.

BACKGROUND OF THE INVENTION

A problem in the development of TTSs is the guarantee of a contour-sealing bond with the skin when wearing the product for periods of a few hours up to 7 days or more. Contour-sealing in this connection means that detachment of an outer edge of the TTS from the skin is avoided.

Effects on the wearing behaviour originate from the size of the TTS and from the administration site on the human body. The mechanical forces acting on the TTS (e.g. stretching, compression, torsion and shear forces), which can lead to detachment from the skin, substantially result from these two parameters.

In order to guarantee that a TTS adheres to the skin for comparatively long periods, an optimization of the adhesive layer facing the skin is necessary. Depending on the construction of the TTS, this layer can be active substance-containing and moreover can contain pharmaceutical auxiliaries which favour the dermal permeation of the active substance. In such cases, the adhesive behaviour of the layer is affected to a greater or lesser extent by the nature and amount of the active agents and auxiliaries contained. Possible further layers of the system may additionally change the state of the layer adhering on the skin side by absorption or release of substances.

A special role is played by the absorption of cutaneous excretions by the TTS. These comprise excretions of gaseous water (transpiration), of liquid water (sweat), of salts (sweat) and of lipids (sebaceous matter). The absorption of water, in particular, leads to a diminished cohesion and shear resistance of the internal structure, whereby the adhesive strength can become reduced even to detachment. Furthermore, considerable and unforeseen changes of the inner structure of the TTS with regard to cohesion, shear resistance and adhesive power may occur as a consequence of individual components being released to the site of application.

In summary, the establishment of optimum adhesive properties is an object mainly concerning the formulation of the adhesive layer and moreover depends strongly on the internal and external construction of the TTS. The variabilities associated therewith make the generalization of successful formulations largely impossible. For each new TTS, a more or less laborious optimization of the adhesive properties is therefore necessary.

Tests on TTSs which are in the development stage are advantageously performed under realistic conditions on humans or animals. Especially when performed on humans, such studies require, however, very high financial expenditure because of the fact that clinical studies frequently fall under the law on drugs, as well as because of the number of individuals required for making clear statistical statements. In addition, experience shows that optimization of adhesive properties constitutes a process that is to be repeated several times in the course of developing a mature product.

For the above reasons, testing on humans takes place only at a late stage of the development. The adhesive strength of TTSs is preferably included as a parameter in clinical studies on therapeutic efficacy and harmlessness. At the early stage of the development, subjective criteria of those persons involved in the development have hitherto played an important part. This development also includes manual testing of the adhesive layer using one's hands, as well as short-term wearing tests on human subjects.

Objectifiable test methods in great part originate from the development of technical adhesives or pressure-sensitive adhesives (cf. official test methods of AFERA; Association des Fabricants Eruopeens de Rubans Auto-adhesifs, Vitry sur Seine, France). In the case of simple mechanical load tests the pressure-sensitive adhesive formulation to be tested is initially applied to a layer-shaped carrier with which it forms a firm composite. This adhesive tape-like test product is then stuck on test surfaces, and subsequently peel forces, for example, which act at varying peel-off angles and speeds, are determined. Given a suitable experimental array it is also possible to determine the tendency of an adhesive compound to flow under mechanical load (cold flow) due to a lack of cohesion.

Testing may be performed within wide limits by variation of parameters such as the properties of test surfaces, as well as temperature and air humidity. The individual tests, however, physically reflect only fractions of the dynamic loading process on the skin. In particular, it is difficult or even impossible to simulate an exchange of substances between the system and the subject wearing it. The mechanical loads are one-sided and virtually always aim at an extreme load on the adhesive, which is not common on the skin.

In summary, these methods are primarily suitable as a means for quality control to quarantee the uniformity of a product and less for optimizing the properties thereof in the development stage.

There are also further methods available for a differentiated assessment of the adhesive properties which typically are much more complicated technologically. For example, by measuring the wetting angles between drops of various test liquids and the surface of a pressure-sensitive adhesive it is possible to obtain data on the surface characteristics of the adhesive. In this way it is possible to detect the energetic relationships and, in particular, the distribution of chemically polar and nonpolar interactions at the outside of the adhesive. Ideally, these relationships are the same as those existing at the surface to be adhered, i.e. the skin in the case of a TTS. By means of this process one can ascertain the physico-chemical affinity of an adhesive to an application surface; the mechanical properties, such as, for instance, the capacity of conforming rapidly to a rough surface, are, however, left entirely out of consideration.

The mechanical, internal properties of adhesives are particularly the subject of methods employed in rheology and in dynamic mechanical analysis (DMA). With the aid of rheometers it is possible to carry out examinations on thin layers of adhesive under action of torsion forces. The type of torsion load as well as the temperature and air humidity during the test can be varied within wide limits. In DMA, in addition to exposure to torsion forces, it is also possible to expose the test material to bending, stretching and compression forces.

Both methods are very well suited for testing the cohesion and shear strength, especially when involving a change in temperature. Furthermore, it is possible to make statements on the cold flow, as well as on elastic and plastic proportions in the deformation of an adhesive mass. The methods are efficient but technically complicated. Nevertheless, they only take into account the internal properties of an adhesive, while the properties of the outer surfaces, as well as the actual tack, are not recorded. An exchange of substances with the environment, as takes place in the case of TTSs worn on the skin, can not be realized employed today's equipment.

Summarizing, there exists a broad range of test methods which, however, always permit statements to be made only on relatively narrow partial aspects of adhesion on the skin. The gathering of the data takes place under strongly abstracted conditions which aim at ascertaining individual physico-chemical characteristic values in their purest form.

There is a lack of realistic test methods and models which make it possible to simulate the wearing of TTSs on the skin in a less abstracted manner and representing the problems entailed as comprehensively as possible. Consequently, there is a demand to realize such a model without great technical effort and in a manner enabling wide-range use for routine testing.

SUMMARY OF THE INVENTION

The object of the invention is to provide a process and a test equipment that enable the testing of the pressure-sensitive adhesive behaviour of flat materials on human or animal skin under realistic conditions, and which enable the determination of the pressure-sensitive adhesive formulations which are optimally suitable for each active substance composition for this purpose.

This object is achieved according to the invention by means of a test method according to the features of claim 1 and a device according to the features of claim 15. The results obtained by this method reflect a good coincidence with the problems of detachment occurring when a TTS is worn on the skin. In conjunction with objective evaluation processes, the test method according to the invention exhibits an astonishingly great capacity for differentiation.

For the testing technique according to the invention, either the entire TTS is used or only a portion thereof. The term portion is to be understood to mean a flat-shaped partial piece separated from the TTs and whose layer structure is identical with that of the TTS. However, a portion may also be a flat material whose layer structure only partially corresponds to that of the TTS and whose outer shape is congruent with that of the TSS or is different therefrom. In any case, the TTS and the portion thereof which is possibly to be tested have an identically formulated pressure-sensitive adhesive layer and at least one further layer possibly different from the other one. The term TTS as used in the following also comprises portions of a TTS in accordance with the above definition.

The TTS to be tested is initially adhered to a piece of a sheet-like, elastic carrier. In all cases the TTS has a smaller surface area than the carrier and is adhered in such a manner that it is located on all sides at a distance from the edge of the carrier. The carrier is disposed, along with the TTS, in the manner of a separating membrane between two half-shell elements. The two half-shell elements are congruent along their edges and, when assembled, enclose a defined internal space—in principle, similarly to the shells of a walnut. The relative volumes enclosed by the two halves may be equally large or differ from each other.

The two shells are held against each other in a tight and contour-sealed manner by appropriate means. The carrier, with the TTS, is fixedly positioned between the two halves in a crease-free, planar and at most slightly pre-stretched manner. This device will in the following be referred to as "test cell". The entire TTS is located within the test cell and is maintained at a distance from the walls on all sides thereof.

In the course of the test procedure, the carrier, along with the TTS located thereon, is recurrently loaded and unloaded. With time, this loading extends over the entire surface of the carrier and is preferably effected from the surface of the carrier facing away from the TTS. This corresponds to the conditions present when wearing the system on the skin, due to the fact that the mechanical load is transferred from the adhered surface to the TTS. The mechanical loading of the carrier can be performed by means of a plunger reciprocating like a piston and which is introduced through a corresponding aperture into the test cell. Preferably, however, the loading is effected by means of a solid body moving circularly, at low speed, on the surface facing away from the TTS. This body is located entirely within the test cell and impresses itself into the elastic carrier, thus effecting the stretching thereof. This stretching does not go beyond the elastic deformability of the carrier, so that practically no deformation occurs. The deformations of the carrier are transferred to the TTS mainly as shearing, stretching, compression, bending and flexure forces.

The rotation of the above mentioned body about an axis, lying within or outside the body, as well as the contact pressure it exerts on the TTS carrier can be brought about in different ways. In one variant, the body is freely rollable and rests on the surface of the TTS carrier only through gravity. The rolling of the body is then effected by tilting the test cell against gravity, and the contact pressure results from the weight and the supporting surface of the body.

In a preferred assembly, contact pressures and movement of the rollable body are determined by an outer, variable magnetic field.

Finally, movement may be imparted on the body from outside the test cell by suitable mechanical connecting elements (e.g. a rod-like axle or a connecting rod).

In summary, chronologically recurring mechanical loading of the TTS takes place, which may be extended for hours or days.

The particular efficiency of the model consists in linking the mechanical load with an exchange of substances between the TTS and its environment. This exchange of substances is made possible by the fact that the two halves of the test cell, which in the most simple case contain air, can also be filled completely or partially with liquid, semi-solid or solid substances.

For example, the transpiration of the skin can be simulated by filling that half of the cell which is opposite the TTS entirely or partially with water or an aqueous solution. If a water-impermeable but water vapour-permeable carrier has been selected, the water can intrude into the TTS in the form of water vapour. The nature and extent of this "transpiration" can be controlled within wide limits by selecting the carrier film, the temperature and osmotically active additives to the water phase. If a microporous carrier film is used, it is even possible under these conditions to contact the TTS with liquid water and with substances possibly dissolved therein. This corresponds to sweating through the pores of the skin.

Furthermore, it is possible to also achieve, parallelly to a mechanical load, a continuous release of substances from the TTS. This is made possible by completely or partially filling that half of the test cell lying opposite the TTS with a medium capable of absorbing, by diffusion, low-molecular ingredients of the TTS. Here, the nature and extent of the diffusion can also be influenced by selecting the carrier film interposed between the two halves. In such a manner, the release from the TTS of a low-molecular substance, a permeation-enhancing auxiliary substance or a plasticizer can be simulated, for example. In practice, the adhesive behaviour of a TTS worn on the skin can be changed considerably and unforeseeably by such processes. In the model according to the invention, such processes can be combined with mechanical influences in a simple manner. Finally, the half of the test cell facing towards the TTS can be filled with liquid too. The liquid then comes into direct contact with the TTS. In this way, where water or diluted aqueous solvents are used, it is possible to simulate the influences that washing, taking a shower, taking a bath or swimming have on the adhesive behaviour of a TTS being worn on the skin.

The evaluation of the tests using the above described model can be performed qualitatively and quantitatively. In qualitative evaluation, the period of time is recorded after which the TTS has become completely debonded from the carrier. In the most simple case, this evaluation can be effected by visual observation at intervals, with the possibility that the exact point in time will not be detected.

For accurate detection of the point in time of complete detachment, an optical control device is mounted on or inside the model. Preferably, this is a signal-modulated light barrier in the visual or the infrared range. The test cell is arranged relative to the light barrier such that a completely detached TTS falls in the direction of gravity, passes through the light beam and interrupts the same.

As an alternative to an optical controlling device, the test cell is equipped such that the TTS falling in the direction of gravity interrupts or closes an electric circuit. To close an electric circuit it may be necessary to provide the TTS with at least one electrically conductive layer, which may be formed of metal or conductive polymers.

Finally, complete detachment of a TTS from the carrier may also be detected by measuring the conductibility between TTS and carrier. The electric resistance is increased continuously during the detachment of the TTS, and shows a sharp rise when the TTS becomes completely detached.

For a more differentiated evaluation of the tests, the quantitative determination of the debonded surface of the TTS is preferred. This is performed at one or several points in time before the TTS has become completely detached. The above mentioned conductibility measurement can be utilised to this end, too, since the conductibility between carrier and TTS is proportional to the contact surface area thereof. In this way, the degree of detachment can be continuously recorded.

In a discontinuous method, the test is discontinued after a defined period of time, and the TTS is removed from the test cell along with the carrier. Those parts of the TTS that have become detached from the carrier material can be coloured with a colouring solution or suspension. By contrast, where the bond between the TTS and the carrier still exists, the dye solution can not reach the surface of the TTS or the carrier and can not colour the same. In this manner, only those detached portions can become dyed which are in direct contact with the edge of the TTS. Detachments enclosed on all sides by remaining contact surfaces are not detected.

BRIEF DESCRIPTION OF THE DRAWINGS

In the following, an example of a preferred assembly of the test apparatus will be illustrated with reference to the Figures.

FIG. 4 shows a lateral cross-sectional view of a test cell for use with a water-permeable carrier film.

FIG. 5 shows a lateral cross-sectional view of a test cell providing direct contact with a liquid medium during a test.

FIGS. 6a–6c schematically illustrate, in a lateral cross-sectional view, the detachment of the TTS from the carrier film.

FIG. 7 illustrates, in a lateral cross-sectional view, the detachment of the TTS when the circular, full-surface TTS does not have a central supported surface.

DETAILED DESCRIPTION OF THE INVENTION

Figure 1:
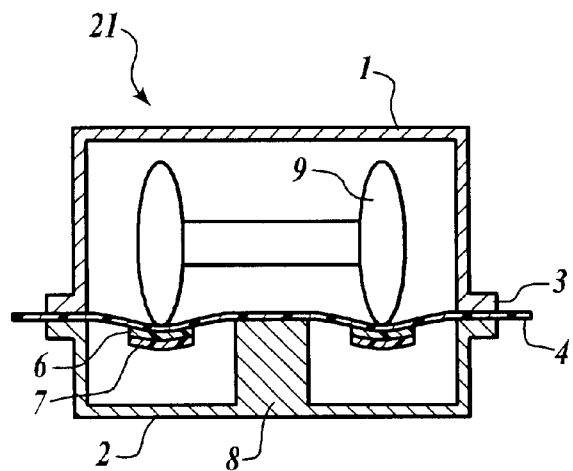
FIG. 1 shows a circular test cell in lateral cross-section.
Figure 2:
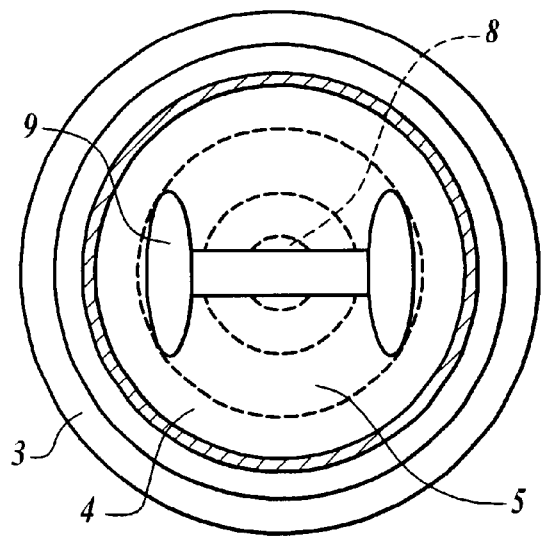
FIG. 2 shows a circular test cell in plan view.

In a preferred embodiment both half-shells (1,2) of the test cell (21) are made of glass. The circular test cell (21) is shown in FIG. 1 in lateral cross-section, while FIG. 2 is a plan view. The test cell (21) consists of an upper (1) and a lower half-shell (2). The upper half-shell (1) preferably encloses a larger volume than the lower one. Both half-shells (1,2) are provided at their edges with a reinforcement (3). The edges of both half-shells (1,2) are congruent and are surface-ground in such a manner that it is possible to place the half-shells (1,2) on each other in a contour-sealed manner. The laterally protruding reinforcement edges (3) permit to mechanically press the half-shells (1,2) together by holding clamps or clips (not shown). Between the half-shells (1,2) there is a carrier film (4) overlapping the cross-section of the shells including the projecting reinforcements (3).

Adhered to this carrier film (4) is the flat material (5), e.g. a TTS, namely on that side of the carrier film (4) which faces towards the bottom part of the test cell (21). The TTS (5) has the shape of a circular ring which is approximately at equal distances from the walls of the test cell (21), and is consequently arranged centrally in the test cell (21). In the simplest case the TTS (5) consists of a pressure-sensitive adhesive layer (6) which adheres to the carrier film (4), as well as of a backing layer (7) covering the adhesive layer (6). In the bottom half-shell (2) of the test cell (21) there is, in centrical arrangement, a cylindrical supporting body (8). The free surface of the body (8) is preferably surface-ground and lies in the same plane as the surface-ground edges (3) of the lower half-shell. When the half-shells (1,2) have been assembled, with interposed carrier film (4), the supporting body (8) forms a support surface for the carrier film (4). The distance between the edge of the supporting body (8) and the edge of the circular hole in the TTS preferably corresponds to the distance between the outer edge and the inner wall of the test cell (21). Within the upper half of the test cell (21) there is a dumbbell-shaped stirring element (9) resting, by gravity, on the, planar, surface of the carrier film (4) facing away from the TTS (5). The stirring element (9) may preferably be a standard product as used for laboratory requisites. It has a smooth and soft surface, e.g. of Teflon. The distance between the two contact surfaces of the stirring element (9) on the carrier film (4) preferably corresponds to the mean value of outer and inner diameter of the flat material which is in the form of a TTS (5). If the test cell (21) is placed on a magnetic stirring unit with support plate, the stirring element (9) in the test cell (21) can be rotated in a circular motion about the centre of the cell. Preferably this takes place at a speed of 1 to 30 revolutions per minute. In such an assembly the contact pressure exerted by the stirring element (9) on the carrier film (4) is the sum of the weight of the stirring element (9) and the attractive force of the magnetic stirring unit acting on it. The magnetic properties of the stirring element (9), as well as the magnetic stirring unit thus have an influence on the test result and must be standardised. During the test, the two contact surfaces of the stirring element (9) follow a circular path on the carrier film (4). The centre of this circular path preferably corresponds to that of the TTS (5). In the region of the contact surfaces a temporary elastic stretching of the carrier film (4) occurs, which conveys itself to the pressure-sensitive TTS disposed at the counter face of the carrier film. In the course of the test this load leads to detachment of a greater or lesser degree, up to complete detachment, of the TTS (5) from the carrier film (4).

Figure 3:
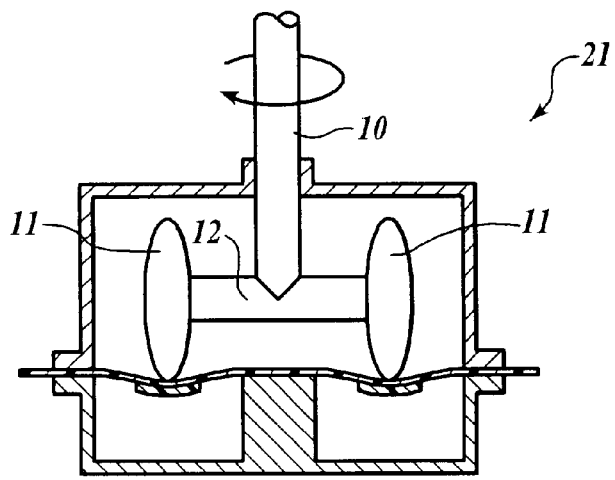
FIG. 3 shows a lateral cross-sectional view of an alternative test device implementing a mechanical transfer rather than a magnetic transfer.

In an alternative assembly of the test set-up, magnetic power transfer is relinquished in favour of mechanical transfer (FIG. 3). The body putting a load on the TTS, said body again being dumbbell-shaped, is now caused to rotate by a shaft (10) introduced from outside. The two end pieces (11) of the stirring element (9) are preferably supported in a freely rotatable manner at the transverse axle (12) thereof, so that they can roll on the carrier film (4) when the stirring element (9) is rotated. The penetration depth of the stirring element (9) into the carrier film (4) can be adjusted by means of the shaft (10).

Selecting a circular TTS (5) in conjunction with the central support body (8) in the bottom half of the test cell results in a particularly favourable load geometry. In conjunction with the dumbbell-shaped stirring element (9) the TTS (5) can be loaded until complete detachment from the carrier film (4) occurs. This detachment process is successively illustrated by FIGS. 6a to 6c. In the case of a circular, full-surface TTS not having a central supported surface, loading by use of the dumbbell-shaped magnetic stirrer leads only to the detachment of the TTS (FIG. 7). This embodiment, however, constitutes a comparatively ineffective assembly. Furthermore, due to the TTS having a circular ring shape as compared to a full-surface embodiment, the ratio of the edge region to the internal surface is increased. The ratio between the surface in the process of becoming detached and the surface still adhering is thereby increased too, so that the differentiation capacity of the model increases. Finally, the circular ring shape reduces the probability of central detachments that lie entirely within the surface of the TTS and which are not accessible to a preferred quantification technique.

The material quality of the carrier film is of particular significance for the test result. Preferred materials are polymers having marked elasticity and good water vapour permeability, while at the same time being practically insoluble in water. These properties are shown, in particular, by polyurethanes and ethyl vinyl acetate copolymers as well as silicone rubbers. Polyethylene and polypropylene as well as the block polymers styrene-isobutylene-styrene (SIS) and styrene-butadiene-styrene (SBS) are available with sufficient elasticities. Their water vapour permeability is, however, low and hardly suitable for simulating the transpiration of the skin.

Suitable carrier materials for the TTS are also human and animal skin. This can be used as full-thickness skin or in the form of isolated skin layers. However, such biogenic carriers, which are difficult to standardize, are not preferred by the invention since they are not suitable for standardized routine testing in a conventional laboratory.

If a water-permeable carrier film (4) is used, the transpiration of the skin can be included in the test procedure by completely or partially filling the upper part of the test cell (21) with water or an aqueous solution. This is done by initially filling the lower half-shell (2) with liquid and assembling the test cell (21) with the cell being turned upside down. Thereafter, the cell is turned over so that the liquid comes into contact with the carrier film (4) and covers the same completely or partially. Such an assembly is shown in FIG. 4. The liquid (13), in the following designated as medium A, in this case covers the carrier film (4) completely. Preferred liquids are water or isotonic sodium solution.

By means of the assembly according to FIG. 4 it is furthermore possible to simulate the release of low-molecular substances (molecular weight up to 1000 Da) from the TTS in or through the skin while the system is being worn, provided that a carrier film (4) is used that has sufficient diffusibility for these substances. Here, the term substances is to be understood as meaning, in particular, active substances as well as permeation enhancers and plasticizers. The two latter groups are available in large number for the formulation of TTSs and are known to those skilled in the art. Should these substances be slightly soluble in the pure, aqueous medium A, other liquids are suitable too. In particular, these are mixtures of water with mono- or polyvalent alcohols, polyethylene glycols or polyvinyl pyrrolidone. As solvents, anionic, cationic, amphoteric or non-ionic surface-active agents can be contained. Also, proteins, preferably serum albumins of humans or animals, may be used for this purpose.

In a further test set-up a water-insoluble film, which is, however, water-permeable through micropores (pore diameter below 100 $\mu$m), is used as the carrier. Microporous polyethylene or polypropylene film is mentioned by way of example. Preferably, the pores of this film are treated with a hydrophylizing agent in order to facilitate the passage of liquid water. If a set-up according to FIG. 3 is used, the medium A, via the pores, comes into direct contact with the TTS. This corresponds to sweating on human skin, where liquid water along with salts is released by glands of the skin via pores to the surface of the skin. It is in particular this form of water contact which in many pressure-sensitive adhesives leads to a deterioration of the adhesive properties, respectively to a detachment of the skin under formation of a moisture film forming between the adhesive layer and the skin.

Finally, with the test set-up according to FIG. 5 it is possible to bring the TTS into direct contact with liquid (medium B), from the outside and during the test. Medium B (14) preferably is water or a solution of surface-active agents in water, so as to simulate the effects of washing, showering, bathing or swimming on the TTS.

Figure 8A:
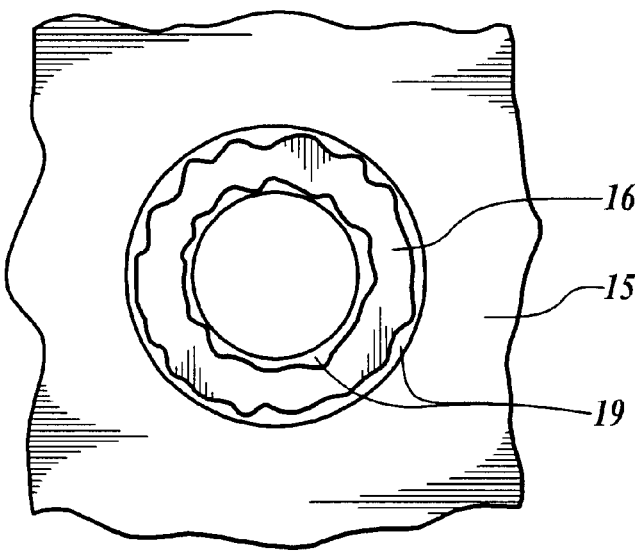
FIGS. 8a–8c schematically illustrate the results of test procedures quantifying the detached surface of a TTS in ratio to the overall surface of the TTS.
Figure 8B:
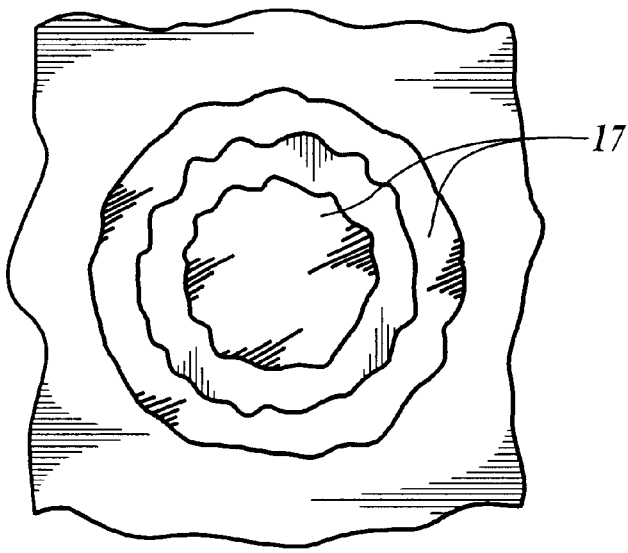
Figure 8C:
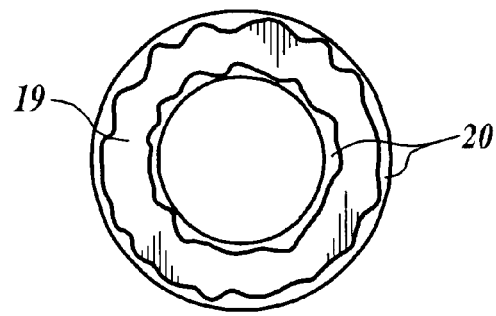

The evaluation of the test is performed by quantification of the detached surface of the TTS in ratio to the overall surface of the TTS. The procedure described in the following is illustrated by FIGS. 8a to 8c. The carrier film (15) and the still adhering TTS (16) are removed from the test cell at the end of the test. Drops of a dye solution (17) are put on the edges of the TTS; the dye solution (17) is capable of entering into the cavities which have formed between the TTS and the carrier film (18) due to detachment. The dye must be capable of colouring either the carrier film or the adhesive layer of the TTS. By contrast, the backing layer of the TTS (that layer of the TTS being located farthest from the carrier film) must be practically uncolourable by the dye for a short time (5 to 10 minutes). After a short duration of action (5 to 10 minutes) the excess dye solution is wiped off with a cloth. If required, the backing layer of the TTS is briefly after-cleaned with the solvent of the dye solution. The dyed surface of the carrier film which projects beyond the surface of the TTS is removed. This is done by punching off excessive carrier film. The punching tool used therefor is the identical tool that was originally used for shaping the TTS. At the end of the procedure, a circular ring-shaped TTS (19) is obtained, which partially adheres to a carrier film of the same geometry. Only the detached surface parts (20) have been coloured by the dye and are thus accessible to further evaluation.

In the simplest case, this evaluation is performed by photocopying the dyed TTS at full scale or at another, defined scale, onto a paper having uniform weight per unit area. The coloured surfaces are cut out from the photocopy and their portion of the overall surface of the TTS is ascertained. Compared to this inaccurate and laborious method, it is preferable to perform the evaluation by computer-aided image processing. To this end, the image of the dyed TTS is produced by means of a conventional scanner or a digital camera (CCD camera), and is converted into a computer-readable form. In this image, it is then possible to perform a computer-aided calculation of the ratio of the dyed surface to the total surface, and thus of the detached portion of the TTS. For this purpose, a large number of computer programs are available to those skilled in the art (e.g. LECO 2003 by LECO Corporation, Image Analysis Group).

The results obtained with the test set-up and test procedure show the high informative value of the test method and reflect in a surprisingly reproducible manner the phenomena of detachment of a TTS from the skin.

TTSs were tested which were made up only of a monolithic layer of adhesive and a backing layer. The backing layer preferably consisted of a transparent film (Hostaphan® RN by Hoechst). As carrier film, a 51-μm-thick EVA film having a portion of vinyl acetate (MSP 98792 by 3M) of 9% was used. The test duration was 24 hours. As dye solution, the saturated solution of Solvent Red 19 in ethanol was used. The evaluation was effected by means of a Sony CCD colour camera on a stand with connected image processing system LECO 2003, on a conventional PC.

In detail the test results were as follows:

1. The uncrosslinked acrylate adhesive Durotek 1051 shows a clearly larger detachment surface than the crosslinked adhesive of the same type (Durotak 1052).

2. At n=2, uncrosslinked adhesive Durotek 1051 and graded additions of crosslinking agent were tested. If no Al is added, this identically results in 6% of detached surface, with 0.01% of Al the detachment is at 4.5%, and with 0.05% of Al it is finally at 3%. This is in accord with the optimum additions of crosslinking agent known for this adhesive from 0.01 to 0.05% of Al.

3. The addition of 1% of Eudragit E100 to Durotak 1051 leads to a physical crosslinking which is already clearly distinguishable by a diminished detachment.

4. When microporous PE film was used as carrier, hot-melt formulations based on ethyl cellulose already after 1 hour exhibited extreme water absorption and almost complete detachment (in accordance with FIG. 4 the upper half of the test cell was filled with water). The moisture sensitivity of these systems had already been known from wearing tests. Further, three of these formulations were tested on an EVA film and again under action of water (this time only water vapour). The extent of the detachment coincided in order with the experience from wearing tests. One of the systems proved to be particularly inadequate and stood out in the test for a special effect: the matrix, which had initially been opaque, was clear as glass in the end, which proved that water absorption had taken place during the test procedure.

5. Moisture-sensitive TTSs were tested on a microporous PE film with and without action of water (according to FIG. 4). It was only under action of water that a partial detachment took place, and the TTS could subsequently be peeled off the carrier very easily. By contrast, the system tested under dry conditions showed practically no detachment and could be manually detached from the carrier only with great difficulty.

What is claimed is:

1. A process for ascertaining the adhesive behavior of pressure-sensitive adhesive flat materials, comprising:

applying said adhesive flat material to an elastic carrier film such that said adhesive flat material adheres to said elastic carrier film;

enclosing said carrier film having said adhesive flat material adhered thereon in a test cell comprising an upper and a lower compartment having congruent edges, wherein said carrier film is interposed between an upper and a lower compartment of the test cell such that it lies within an internal chamber formed by both compartments of said test cell;

subjecting said carrier film having said adhesive flat material adhered thereon to one or more mechanical stresses or repeated mechanical stresses; and, evaluating the degree of detachment of said adhesive flat material from said carrier film in response to said mechanical stress.

2. The process according to claim 1, wherein the forces causing said mechanical stress are exerted onto a surface of said carrier film which faces away from the surface to which said adhesive flat material adheres.

3. The process according to claim 1, wherein enclosing said carrier film having said adhesive flat material adhered thereon in a test cell further comprises clamping said carrier film between a reinforcing edge of the upper compartment and a reinforcing edge of the lower compartment such that said internal chamber is hermetically sealed and the carrier film is retained between said upper and lower compartments and the adhesive flat material adhered to said carrier film is maintained at a distance from said internal chamber on all sides thereof.

4. The process according to claim 1, wherein said carrier film is arranged such that within said test cell such that it is supported by a central support member of one of the compartments.

5. The process according to claim 1, wherein said mechanical stress is exerted periodically onto a surface of said carrier film which is opposite to the adhesive flat material adhering to the film, and comprises stretching of said carrier film by means of a rotary element pressing onto said carrier film.

6. The process according to claim 5, wherein said rotary element comprises one or more magnetic rotary elements wherein said rotary element(s) are rotated by a magnetic field generated by one or more magnetic stirring units.

7. The process according to claim 5, wherein the rotary element comprises a rollable body controllably rotated by one or more undulating control mechanisms whereby the rollable body rolls onto the laminate in response to gravitational forces induced by the tilting of the test cell imparted by the one or more undulating control mechanisms.

8. The process according to claim 1, additionally comprising exposing said elastic carrier f film to one or more liquid medium(s) wherein the liquid medium is introduced into one of the compartments such that the liquid medium is in contact with the elastic carrier film during the process, and said one compartment being the compartment which is opposite to the side of the carrier that carries said adhesive material.

9. The process according to claim 8, wherein the one or more liquid medium(s) comprise an aqueous solution selected from the group consisting of water, osmotically active additives, monovalent alcohols, polyvalent alcohols, polyethylene glycols, polyvinyl pyrrolidone, anionic, cationic, amphoteric, nonionic surface-active agents and proteins.

10. The process according to claim 9, wherein the elastic carrier film comprises microporous polyethylene or microporous polypropylene.

11. The process according to claim 1, additionally comprising exposing said elastic carrier film and said adhesive flat material adhered thereon to one or more liquid medium (s) wherein the liquid medium is introduced into one of the compartments such that the liquid medium is in contact with the adhesive flat material, and wherein said liquid medium is water or an aqueous solution.

12. The process according to claim 1, wherein the step of evaluating comprises optically detecting the degree of separation of the adhesive flat material from the carrier film.

13. The process according to claim 12, wherein the step of evaluating comprises removing the carrier film with the adhesive flat material from the test cell after subjecting it to mechanical stress; adding one or more dyes to said carrier film, said dye being capable of selectively coloring either the adhesive flat material or the elastic carrier film such that the dye infiltrates and colors a plurality of cavities formed between the detached portions of the adhesive flat material and the elastic carrier film; and, measuring the dyed surface relative to the non-dyed surface area of the adhesive flat material by computer-aided image processing.

14. The process according to claim 13, wherein the computer-aided image processing comprises acquiring an electronic image generated by a scanner or digital camera and computer-aided calculation of a ratio of the dyed surface to the non-dyed surface.

15. The process according to claim 1, wherein the adhesive flat material used in the process is formed as a circular ring-shaped flat material.

16. The process according to claim 5, wherein the speed of rotation of the rotary element is between 1 and 30 rpm.

17. A device for ascertaining the adhesive behavior of pressure-sensitive adhesive materials, comprising:

an upper compartment having a first reinforcing edge and a bottom compartment having a second reinforcing edge, wherein the first and second reinforcing edges are releasably retained in tight association to form a test cell having an internal chamber, and wherein said edges serve to fix an elastic carrier film between said compartments, to which carrier film said adhesive material is initially adhered when the device is assembled;

a rotary element which is present within one of said compartments, wherein the rotary element is arranged such that it contacts said carrier film and exerts, in a chronologically repeated sequence, controllable pressure onto said carrier film, thus causing recurrent elastic deformation of said film and subjecting said adhesive material adhered to said carrier film to repetitive mechanical stress, whereby said adhesive material becomes detached from said carrier and the degree of detachment is evaluated for ascertaining the adhesive behavior of the adhesive material; and drive means located outside of said compartments and interacting with said rotary element, thus causing said rotary element to rotate.

18. The device according to claim 17, wherein the lower compartment further comprises a raised, centrally disposed support member having a support surface that is in the same plane as the second reinforcing edge and is arranged such that the carrier film, when fixed between the edges of the compartments, is in contact with the support surface.

19. The device according to claim 17, wherein the rotary element comprises one or more magnetic rotary elements, and wherein said drive means comprises one or more magnetic stirring units.

20. The device according to claim 17, wherein the rotary element is connected to a stirring shaft which is mechanically driven by the drive means, which comprises a motor.

21. The device according to claim 17, wherein said compartments are made of glass or transparent plastic, and wherein said reinforcement edges form a pair of complementary circumferential flanges.

22. The device according to claim 17, further comprising one or more apertures in either or both of the upper or lower compartments for filling and draining of liquids.

* * * * *